United States Patent
Wham et al.

(10) Patent No.: US 9,782,212 B2
(45) Date of Patent: Oct. 10, 2017

(54) HIGH LEVEL ALGORITHMS

(71) Applicant: COVIDIEN LP, Mansfield, MA (US)

(72) Inventors: Robert H. Wham, Boulder, CO (US); William D. Faulkner, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 329 days.

(21) Appl. No.: 14/557,612

(22) Filed: Dec. 2, 2014

(65) Prior Publication Data

US 2016/0151107 A1    Jun. 2, 2016

(51) Int. Cl.
| | |
|---|---|
| A61B 18/12 | (2006.01) |
| G05B 15/02 | (2006.01) |
| A61B 18/00 | (2006.01) |
| A61B 18/14 | (2006.01) |

(52) U.S. Cl.
CPC .......... *A61B 18/1206* (2013.01); *G05B 15/02* (2013.01); *A61B 2018/0063* (2013.01); *A61B 2018/00607* (2013.01); *A61B 2018/00648* (2013.01); *A61B 2018/00702* (2013.01); *A61B 2018/00779* (2013.01); *A61B 2018/00791* (2013.01); *A61B 2018/00827* (2013.01); *A61B 2018/00875* (2013.01); *A61B 2018/00892* (2013.01); *A61B 2018/1455* (2013.01)

(58) Field of Classification Search
None
See application file for complete search history.

(56) References Cited

U.S. PATENT DOCUMENTS

| | | | |
|---|---|---|---|
| 6,948,503 B2 * | 9/2005 | Refior | A61B 18/1206 128/898 |
| 7,722,601 B2 * | 5/2010 | Wham | A61B 18/1206 606/34 |
| 7,972,328 B2 | 7/2011 | Wham et al. | |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

U.S. Appl. No. 14/297,812 dated Jun. 6, 2014, inventor: Wham.

(Continued)

*Primary Examiner* — Ronald Hartman, Jr.

(57) ABSTRACT

A method for operating an electrosurgical generator is disclosed, including receiving a high level algorithm at an electrosurgical generator including a processor, a power supply, and a radio frequency amplifier, the high level algorithm including an interpreted language script, processing the interpreted language script through an interpreter engine executed by the processor, selecting at least one of a plurality of configuration files stored in the electrosurgical generator based on the interpreted language script to effect a desired mode of operation, and executing the interpreted language script based on the selected one of the plurality of configuration files to generate instructions which cause the electrosurgical generator to control at least one of the power supply and the radio frequency amplifier to generate radio frequency energy according to the selected one of the plurality of configuration files.

14 Claims, 5 Drawing Sheets

(56) References Cited

U.S. PATENT DOCUMENTS

| | | | |
|---|---|---|---|
| 8,147,485 B2 | 4/2012 | Wham et al. | |
| 8,216,223 B2 | 7/2012 | Wham et al. | |
| 8,685,016 B2 | 4/2014 | Wham et al. | |
| 2005/0203504 A1* | 9/2005 | Wham | A61B 18/1442 606/34 |
| 2009/0248007 A1 | 10/2009 | Falkenstein et al. | |
| 2009/0248013 A1* | 10/2009 | Falkenstein | A61B 90/90 606/41 |
| 2010/0094285 A1* | 4/2010 | Arts | A61B 17/32056 606/47 |
| 2012/0089139 A1* | 4/2012 | Wham | A61B 18/1206 606/33 |
| 2012/0136354 A1 | 5/2012 | Rupp | |
| 2012/0283731 A1 | 11/2012 | Unger et al. | |
| 2013/0267945 A1* | 10/2013 | Behnke, II | A61B 18/1206 606/34 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206443 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2666432 A1 | 11/2013 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 2006/050888 A1 | 5/2006 |
| WO | 2008/053532 A1 | 5/2008 |

OTHER PUBLICATIONS

U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

(56) References Cited

OTHER PUBLICATIONS

Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.

* cited by examiner

HIGH LEVEL ALGORITHMS

BACKGROUND

Technical Field

The present disclosure relates to a system and method for operating an electrosurgical generator. More particularly, the present disclosure relates to a system, method, and apparatus for using a high level algorithm (HLA) to operate and control an electrosurgical generator.

Background of Related Art

Electrosurgery involves application of high radio frequency electrical current to a surgical site to cut, ablate, or coagulate tissue.

Electrosurgery involves application of high radio frequency electrical current to a surgical site to, e.g., cut, ablate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like. A forceps is a pliers-like instrument which relies on mechanical action between its jaws to grasp, clamp, and constrict vessels or tissue. Electrosurgical forceps (open or endoscopic) utilize mechanical clamping action and electrical energy to affect hemostasis on the clamped tissue. The forceps include electrosurgical conductive surfaces which apply the electrosurgical energy to the clamped tissue. By controlling the intensity, frequency, and duration of the electrosurgical energy applied through the conductive plates to the tissue, the surgeon can, for example, coagulate, cauterize, and/or seal tissue. However, the above example is for illustrative purposes only and there are many other known bipolar electro surgical instruments which are within the scope of the present disclosure.

The electrosurgical procedures outlined above may utilize various tissue and energy parameters in a feedback-based control system. In electrosurgery, there is a continual need to improve delivery of energy to the tissue.

SUMMARY

According to one embodiment, the present disclosure provides for a method for operating an electrosurgical generator.

In an aspect of the present disclosure, the method includes receiving a high level algorithm at an electrosurgical generator including a processor, a power supply, and a radio frequency amplifier, the high level algorithm including an interpreted language script, processing the interpreted language script through an interpreter engine executed by the processor, selecting at least one of a plurality of configuration files stored in the electrosurgical generator based on the interpreted language script to effect a desired mode of operation, and executing the interpreted language script based on the selected one of the plurality of configuration files to generate instructions which cause the electrosurgical generator to control at least one of the power supply and the radio frequency amplifier to generate radio frequency energy according to the selected one of the plurality of configuration files.

In another aspect of the present disclosure, the method includes measuring, at a sensor coupled to the radio frequency amplifier, at least one property of the radio frequency energy.

In a further aspect of the present disclosure, the method includes selecting another mode of operation based on the at least one property of the radio frequency energy.

In yet a further aspect of the present disclosure, the method includes selecting a second one of the plurality of configuration files based on the selected another mode of operation.

In a still further aspect of the present disclosure, the method includes selecting the second one of the plurality of configuration files based on the interpreted language script to effect the selected another mode of operation, and executing the interpreted language script based on the selected second one of the plurality of configuration files to generate instructions which cause the electrosurgical generator to control at least one of the power supply and the radio frequency amplifier to generate radio frequency energy according to the selected second one of the plurality of configuration files.

In another aspect of the present disclosure, the method includes modifying the selected one of the plurality of configuration files to generate a modified configuration file, and executing the interpreted language script based on the modified configuration file to generate instructions which cause the electrosurgical generator to control at least one of the power supply and the radio frequency amplifier to generate radio frequency energy according to the modified configuration file.

According to another embodiment, the present disclosure provides for a system for operating an electrosurgical generator.

In an aspect of the present disclosure, the system includes an external download source configured to provide a high level algorithm to the electrosurgical generator, and the electrosurgical generator including a power supply, a radio frequency amplifier, a processor, and a memory, the processor configured to receive the high level algorithm from the external download source, the high level algorithm including an interpreted language script, process the interpreted language script through an interpreter engine executed by the processor, select at least one of a plurality of configuration files stored in the memory based on the interpreted language script to effect a desired mode of operation, and execute the interpreted language script based on the selected on of the plurality of configuration files to generate instructions which cause the electrosurgical generator to control at least one of the power supply and the radio frequency amplifier to generate radio frequency energy according to the selected one of the plurality of configuration files.

In another aspect of the present disclosure, the electrosurgical generator further includes a sensor coupled to the radio frequency amplifier, the sensor configured to measure at least one property of the radio frequency energy.

In a further aspect of the present disclosure, the processor is further configured to select another mode of operation based on the at least one property of the radio frequency energy.

In yet a further aspect of the present disclosure, the processor is further configured to select a second one of the plurality of configuration files based on the selected another mode of operation.

In still a further aspect of the present disclosure, the processor is further configured to select the second one of the plurality of configuration files based on the interpreted language script to effect the another mode of operation, and execute the interpreted language script based on the selected second one of the plurality of configuration files to generate instructions which cause the electrosurgical generator to control at least one of the power supply and the radio frequency amplifier to generate radio frequency energy according to the selected second one of the plurality of configuration files.

In another aspect of the present disclosure, the processor is further configured to modify the selected one of the plurality of configuration files to generate a modified configuration file, and execute the interpreted language script based on the modified configuration file to generate instructions which cause the electrosurgical generator to control at least one of the power supply and the radio frequency amplifier to generate radio frequency energy according to the modified configuration file.

According to another embodiment, the present disclosure provides for an electrosurgical generator.

In an aspect of the present disclosure, the electrosurgical generator includes a power supply, a radio frequency amplifier, a processor, and a memory, the processor configured to receive a high level algorithm, the high level algorithm including an interpreted language script, process the interpreted language script through an interpreter engine executed by the processor, select at least one of a plurality of configuration files stored in the memory based on the interpreted language script to effect a desired mode of operation, and execute the interpreted language script based on the selected one of the plurality of configuration files to generate instructions which cause the electrosurgical generator to control at least one of the power supply and the radio frequency amplifier to generate radio frequency energy according to the selected one of the plurality of configuration files.

In another aspect of the present disclosure, the electrosurgical generator further includes a sensor coupled to the radio frequency amplifier, the sensor configured to measure at least one property of the radio frequency energy.

In a further aspect of the present disclosure, the processor is further configured to select another mode of operation based on at least one property of the radio frequency energy.

In yet a further aspect of the present disclosure, the processor is further configured to select a second one of the plurality of configuration files based on the selected another mode of operation.

In still a further aspect of the present disclosure, the processor is further configured to select the second one of the plurality of configuration files based on the interpreted language script to effect the another mode of operation, and execute the interpreted language script based on the selected second one of the plurality of configuration files to generate instructions which cause the electrosurgical generator to control at least one of the power supply and the radio frequency amplifier to generate radio frequency energy according to the selected second one of the plurality of configuration files.

In another aspect of the present disclosure, the processor is further configured to modify the selected one of the plurality of configuration files to generate a modified configuration file, and execute the interpreted language script based on the modified configuration file to generate instructions which cause the electrosurgical generator to control at least one of the power supply and the radio frequency amplifier to generate radio frequency energy according to the modified configuration file.

In another aspect of the present disclosure, the processor is further configured to modify to select another mode of operation based on at least one of user input or an identifier associated with an instrument coupled to the power supply. The identifier may be a barcode, a radio frequency identification tag, or a storage device.

Any of the above aspects and embodiments of the present disclosure may be combined without departing from the scope of the present disclosure.

BRIEF DESCRIPTION OF THE DRAWINGS

Various illustrative embodiments of the present disclosure are described herein with reference to the drawings wherein.

DETAILED DESCRIPTION

Particular embodiments of the present disclosure are described below with reference to the accompanying drawings. In the following description, well-known functions or constructions are not described in detail to avoid obscuring the present disclosure in unnecessary detail.

Figure 1:
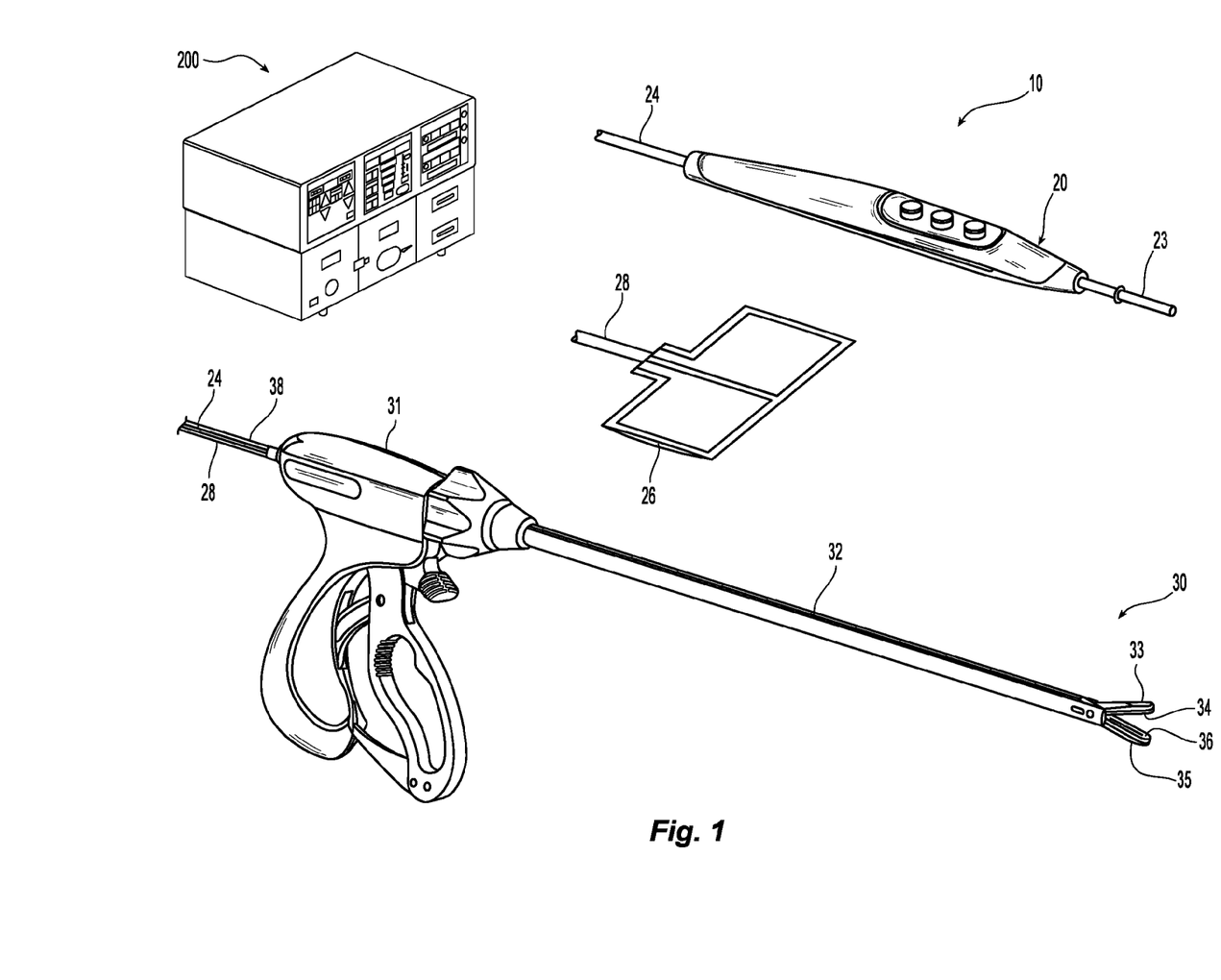
FIG. 1 is a perspective view of the components of an electrosurgical system according to one illustrative embodiment of the present disclosure.

The present disclosure provides for systems and methods for operating an electrosurgical generator to perform any suitable electrosurgical procedure. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., vessel sealing). In embodiments, the generator may be embedded, integrated, or otherwise coupled to the electrosurgical instruments providing for an all-in-one electrosurgical apparatus. The generator may be configured to receive a high level algorithm (HLA) which may be executable by an HLA Engine incorporated within the electrosurgical generator, allowing the electrosurgical generator to modify its operation in real-time FIG. 1 is a perspective view of the components of one illustrative embodiment of a bipolar and monopolar electrosurgical system 10 according to the present disclosure. The system 10 may include one or more monopolar electrosurgical instruments 20 having one or more active electrodes 23 (e.g., electrosurgical cutting probe, ablation electrode(s), etc.) for treating tissue of a patient. Electrosurgical alternating current is supplied to the instrument 20 by a generator 200 via a supply line 24 that is connected to an active terminal 230 (FIG. 3) of the generator 200, allowing the instrument 20 to cut, coagulate, ablate and/or otherwise treat tissue. The alternating current is returned to the generator 200 through a return electrode pad 26 via a return line 28 at a return terminal 32 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
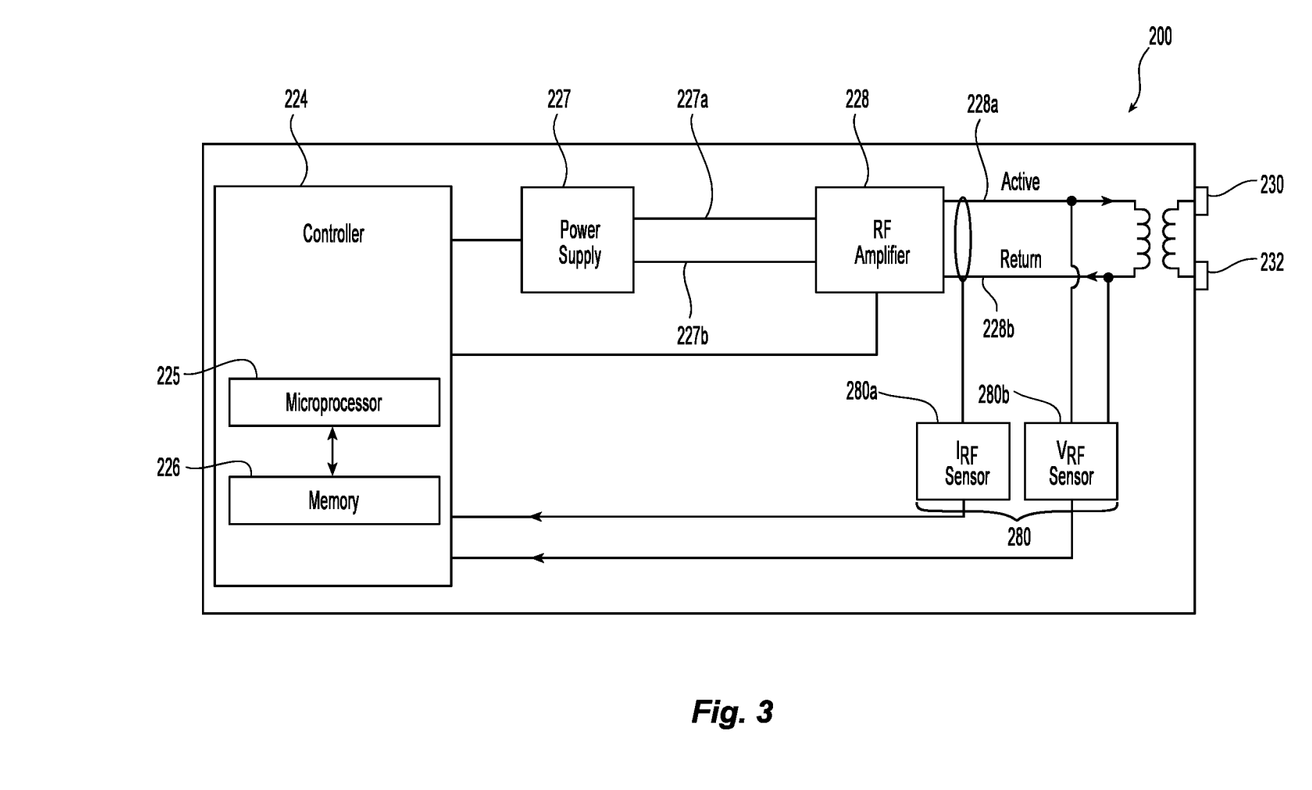
FIG. 3 is a schematic, block diagram of the embodiment of an electrosurgical generator of FIG. 2.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28 coupled to the active and return terminals 230, 232, respectively (FIG. 3). The electrosurgical forceps 30 is coupled to the generator 200 at a connector having connections to the active and return terminals 230 and 232 (e.g., pins) via a plug disposed at the end of the cable 38, wherein the plug includes contacts from the supply and return lines 24, 28 as described in more detail below.

Figure 2:
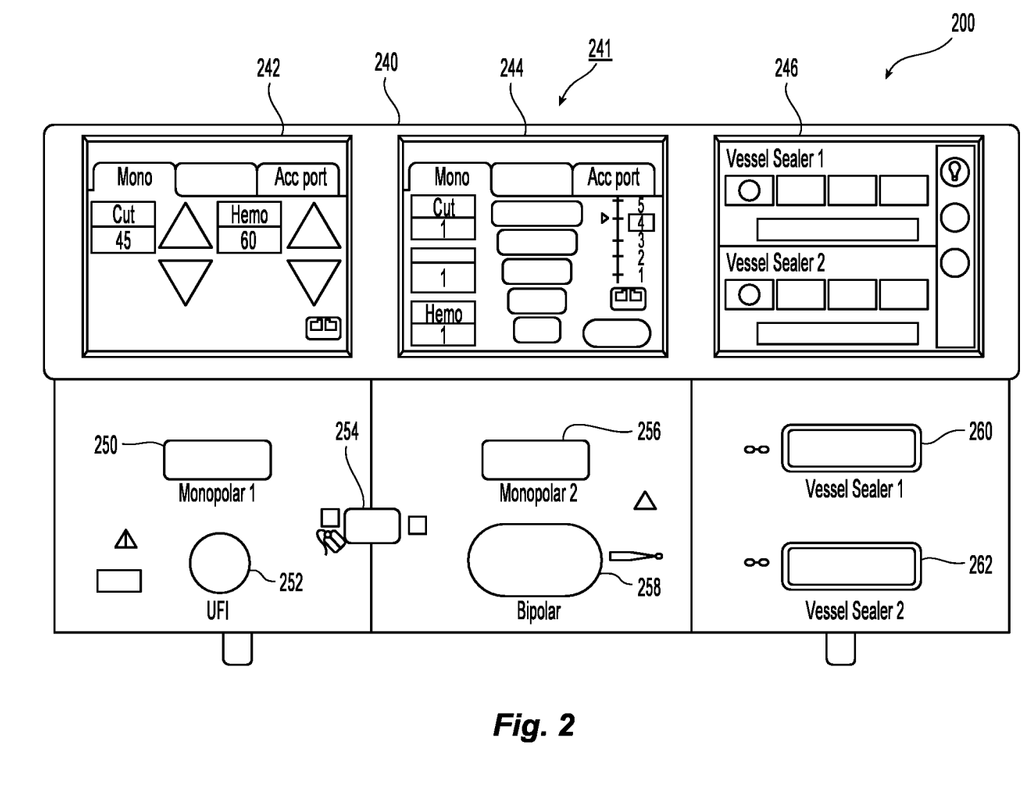
FIG. 2 is a front view of one embodiment of an electrosurgical generator according to an illustrative embodiment of the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 30, etc.).

The generator 200 includes a user interface 241 having one or more display screens or information panels 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 30, etc.). The user then adjusts inputs by simply touching corresponding menu options.

Screen 242 controls monopolar output and the devices connected to the connectors 250 and 252. Connector 250 is configured to couple to a monopolar electrosurgical instrument (e.g., electrosurgical instrument 20) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 30 that may be plugged into the connectors 260 and 262. The generator 200 outputs energy through the connectors 260 and 262 suitable for sealing tissue grasped by the forceps 30. In particular, screen 246 outputs a user interface that allows the user to input a user-defined intensity setting. The user-defined setting is transmitted to the controller 224 where the setting may be saved in memory 226, and may be any setting that allows the user to adjust one or more energy delivery parameters, such as power, current, voltage, energy, etc. or sealing parameters, such as energy rate limiters, sealing duration, etc. In embodiments, the intensity setting may be a number scale, such as for example, from one to ten or one to five. In embodiments, the intensity setting may be associated with an output curve of the generator 200. The intensity settings may be specific for each forceps 30 being utilized, such that various instruments provide the user with a specific intensity scale corresponding to the forceps 30.

Figure 4:
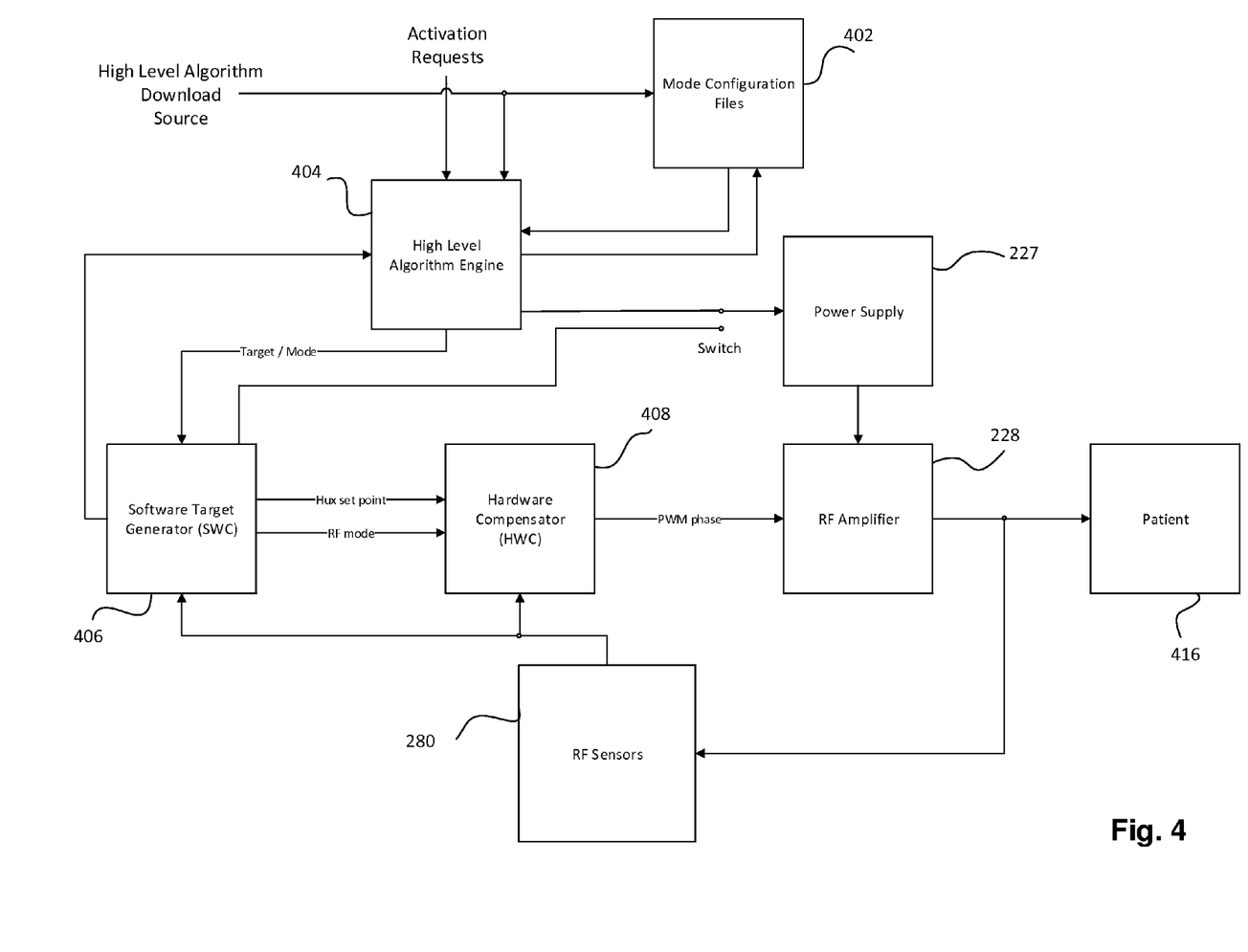
FIG. 4 is a flowchart of an illustrative configuration of the electrosurgical generator of FIG. 2 using a high level algorithm.

FIG. 3 shows a schematic block diagram of the generator 200 configured to output electrosurgical energy. The generator 200 includes a controller 224, a power supply 227, and a radio-frequency (RF) amplifier 228. The power supply 227 may be a high voltage, DC power supply connected to an AC source (e.g., line voltage) and provides high voltage, DC power to the RF amplifier 228 via leads 227a and 227b, which then converts high voltage, DC power into treatment energy (e.g., electrosurgical or microwave) and delivers the energy to the active terminal 230. The output voltage typically ranges from about 50v to 350v, and is controlled by the HLA via a software target generator 406 (FIG. 4). The energy is returned the generator 200 via the return terminal 232. The active and return terminals 230 and 232 are coupled to the RF amplifier 228 through an isolation transformer 229. The RF amplifier 228 is configured to operate in a plurality of modes, during which the generator 200 outputs corresponding waveforms having specific duty cycles, peak voltages, crest factors, etc. The RF amplifier 228 may be a phase shifted resonant inverter topology, with a pulse width modulator (PWM) input and a high voltage, DC input. Adjustments to the PWM phase control the output energy of the RF amplifier 228 such that minimum energy output is associated with low PWM phase shifts while high energy outputs are associated with high PWM phase shifts. The power supply 227 acts as a multiplier to the RF amplifier 228 output, wherein a lower power supply value will case the RF amplifier 228 output energy to be lower than the output with the same PWM phase but at a higher power supply value. It is envisioned that in other embodiments, the generator 200 may be based on other types of suitable power supply topologies.

The controller 224 includes a microprocessor 225 operably connected to a memory 226. Memory 226 may include any non-transitory computer-readable storage media for storing data and/or software that is executable by the microprocessor 225 and which controls the operation of the generator. In an embodiment, memory 226 may include one or more solid-state storage devices such as flash memory chips. Alternatively, or in addition to the one or more solid-state storage devices, memory 226 may include one or more mass storage devices connected to the microprocessor 225 through a mass storage controller (not shown) and a communications bus (not shown). Although the description of computer-readable media contained herein refers to a solid-state storage, it should be appreciated by those skilled in the art that computer-readable storage media can be any available media that can be accessed by the microprocessor 225. That is, computer readable storage media includes non-transitory, volatile and non-volatile, removable and non-removable media implemented in any method or technology for storage of information such as computer-readable instructions, data structures, program modules, or other data. For example, computer-readable storage media includes RAM, ROM, EPROM, EEPROM, flash memory or other solid state memory technology, CD-ROM, DVD, BLU-RAY® or any other optical storage, magnetic cassettes, magnetic tape, magnetic disk storage or other magnetic storage devices, or any other medium which can be used to store the desired information and which can be accessed by the generator.

The microprocessor 225 includes an output port that is operably connected to the power supply 227 and/or RF amplifier 228 allowing the microprocessor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or RF amplifier 228, which adjusts the DC and/or power supply, respectively. Those skilled in the art will appreciate that the microprocessor 225 may be substituted for by using any logic processor (e.g., control circuit) adapted to perform the calculations and/or set of instructions described herein including, but not limited to, field programmable gate array, digital signal processor, and combinations thereof.

The generator 200 according to the present disclosure includes a plurality of sensors 280, e.g., an RF current sensor 280a, and an RF voltage sensor 280b. Various components of the generator 200, namely, the RF amplifier 228, the RF current and voltage sensors 280a and 280b, may be disposed on a printed circuit board (PCB). The RF current sensor 280a is coupled to the active terminal 230 and provides measurements of the RF current supplied by the RF amplifier 228. The RF voltage sensor 280b is coupled to the active and return terminals 230 and 232 provides measurements of the RF voltage supplied by the RF amplifier 228. In embodiments, the RF current and voltage sensors 280a and 280b may be coupled to active and return leads 228a and 228b, which interconnect the active and return terminals 230 and 232 to the RF amplifier 228, respectively. The RF sensors represent the analog and digital hardware and software required to convert the sensed voltage and current RF waveforms delivered to the patient into the representative current, voltage, and power delivered to the patient, as well as the complex patient load impedance.

The RF current and voltage sensors 280a and 280b provide the sensed RF voltage and current signals, respectively, to the controller 224, which then may adjust output of the power supply 227 and/or the RF amplifier 228 in response to the sensed RF voltage and current signals. The controller 224 also receives input signals from the input controls of the generator 200, the instrument 20, and/or forceps 30. The controller 224 utilizes the input signals to adjust power outputted by the generator 200 and/or performs other control functions.

With reference to FIG. 4, a flowchart of a method for using a HLA to operate and control the electrosurgical generator 200 according to the present disclosure is shown. Elements and structures with the same function as shown in FIGS. 1-3 are numbered the same and will not be described again for purpose of brevity. The HLA may be written in an interpreted language which can be executed by a high level algorithm engine (HLA engine) 404. As used herein, "interpreted language" refers to any computer language that is interpreted directly by an interpreter, rather than first being compiled into machine-language instructions. The HLA engine 404 is a language interpreter configured to execute an interpreted language script (HLA script). The HLA engine 404 may be implemented in either software executable by the microprocessor 225 or hardware, e.g., microprocessor 225. The HLA script contains instructions to be executed by the engine and may include any software instructions, such as an RF delivery algorithm, which may be stored on any suitable computer-readable medium, e.g., memory 226. The instructions for performing the various functions of the generator may be contained in pre-compiled subroutines that are called by the HLA script to be executed. Thus, the HLA script may not need to include the specific instructions for causing the generator to perform a particular function, and would instead call on these pre-compiled subroutines for executing those functions. The usage of an interpreted language allows the underlying engine to be created and executed on any microprocessor or digital machine, which may then in turn execute the HLA script, thus making the HLA script highly portable and easily replaceable.

The HLA may be received by the generator 200 from a download source. The download source may be external to the generator 200, such as another computer or server accessible over a network, or internal, such as a memory storage device, for example memory 226 and/or a removable storage medium. Alternatively, the download source may be a cloud-based update server or the like. A handset for use with the generator 200 may incorporate a radio frequency identification (RFID) device, or any other suitable storage medium, which may include its own memory storing a HLA script that the generator 200 may download, and/or instructions to configure the generator to download a particular HLA script from an external source, such as a cloud-based update server. In embodiments, the storage medium may be a barcode including a link to the external source for downloading the HLA. The network may be any network known to those skilled in the art, such as a local area network (LAN) consisting of a wired network and/or a wireless network, a wide area network (WAN), a wireless mobile network, a BLUETOOTH® network, and/or the Internet.

In addition to the HLA, the generator 200 may receive or store, e.g., by preloading, a set of mode configuration files ("CFG files") 402 which control the operation of the generator. The CFG files 402 contain all the information required to generate a specific form of RF energy, which enables the generator 200 to operate in various RF modes, such as, for example, cut, coag, spray, fulgurate, etc. Multiple CFG files 402 may be associated with a single HLA, which allows the HLA to use several modes during execution. The HLA can load a specific CFG file 402 to start RF generation, and then monitor the delivered RF and tissue response and during energy application, a new CFG file 402 may be loaded based on sensed tissue or energy properties as needed. In embodiments, to enter a different RF mode, the HLA may modify the existing CFG files 402 to modify RF energy delivery, e.g., change mode, adjust amplitude, etc., when a specific tissue event occurs. In further embodiments, during execution, the HLA may start treatment using a first mode, e.g., a cut RF mode, and, once cutting is completed, the HLA may then load a second mode, e.g., coag RF mode which then cauterizes the tissue.

Figure 5:
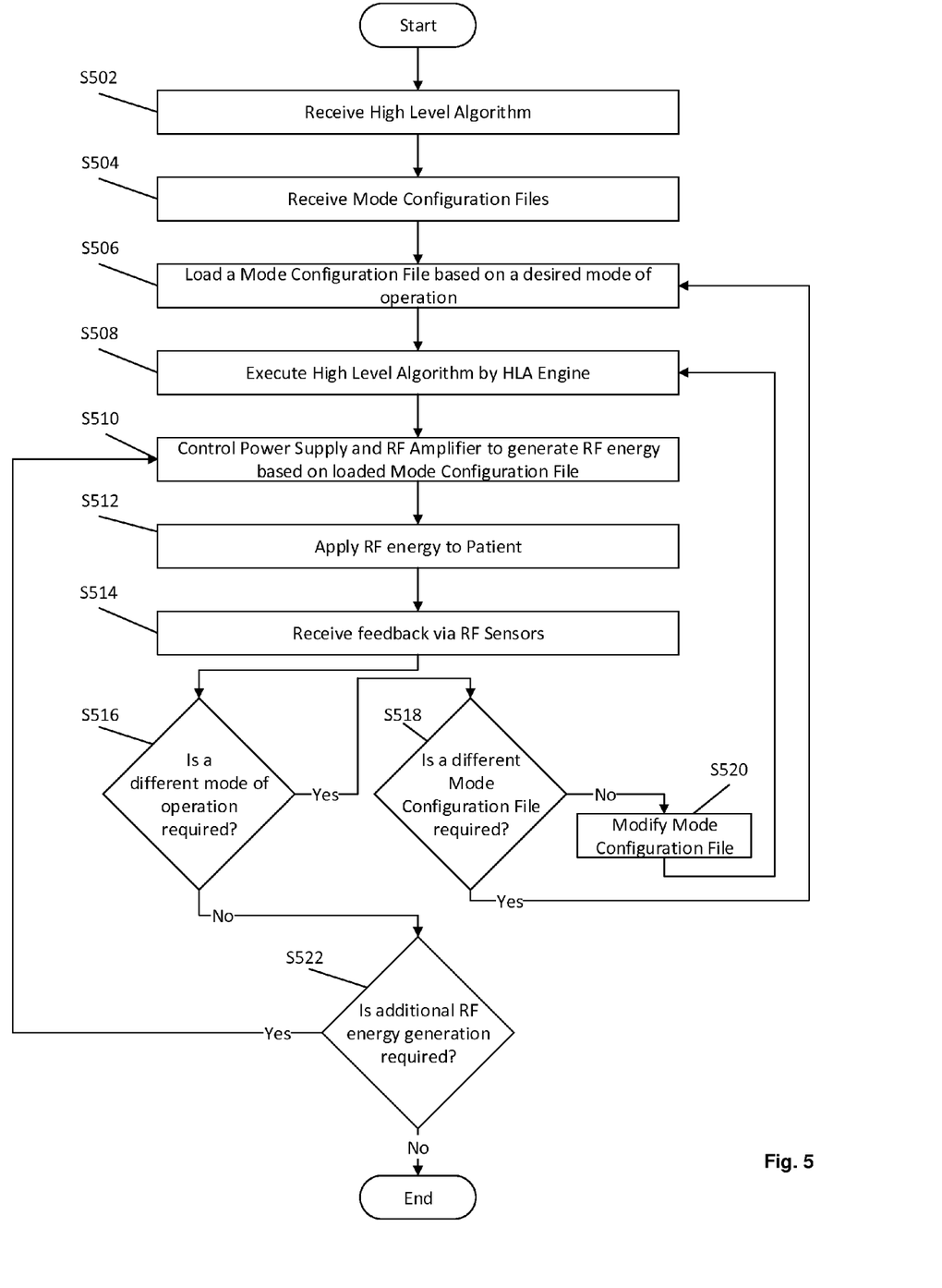
FIG. 5 is a flowchart of a method for operating the electrosurgical generator of FIG. 2 using the high level algorithm of FIG. 4.

During execution of the HLA in conjunction with the CFG files 402, HLA engine 404 sends instructions to a software target generator (SWC) 406. SWC 406 controls the programming of a hardware compensator (HWC) 408, and controls target adjustments so that HWC 408 correctly implements a desired RF energy profile specified by the loaded CFG file 402. HWC 408 is described below as one exemplary embodiment of an RF inverter or output stage and any other suitable inverter may be utilized by the generator 200 according to the present disclosure. HWC 408 in turn controls RF amplifier 228 based on the loaded CFG file 402 to implement the correct configuration and the desired RF energy output range. SWC 406 may be implemented as software executable by a microprocessor, and/or implemented as a hardware component. HWC 408 is designed to adjust the PWM phase shift such that energy is delivered to the patient at the desired RF current, voltage, and/or power. HWC 408 also creates the pulse patterns of the RF waveform. Referring now to FIG. 5, a flowchart is shown of a method for using an HLA to operate and control the generator 200 according to the present disclosure. Processing may start at step S502, when the generator 200 receives an HLA. Receiving the HLA may include one or more of loading the HLA from internal storage, loading the HLA from external storage, and/or downloading the HLA from a source external to the generator 200, such as, for example, a computer connected via a network. At step S504, the generator 200 receives one or more CFG files. Receiving the CFG files may also include one or more of loading the CFG files from internal storage, loading the CFG files from external storage, loading the CFG files from a memory storage device associated with the electrosurgical instrument 20 connected to generator 200, and/or downloading the CFG files from a source external to the generator 200, such as, for example, a computer connected via a network. In embodiments, CFG files may be preloaded in the generator 200, e.g., memory 226. Thereafter, at step S506, a CFG file is selected and loaded based on a desired mode of operation. In one aspect of the present disclosure, if a cut operation is desired, a corresponding CFG file may be loaded to implement a RF energy profile to perform a cut operation. Alternatively, if a coag operation is desired, a corresponding CFG file may be loaded to implement a RF energy profile to perform a coag operation.

At step S508, the HLA is executed by the HLA engine using the loaded CFG file. The execution of the HLA in turn, at step S510, controls the power supply 227 and the RF amplifier 228 to generate RF energy according to the RF energy profile associated with the loaded CFG file. At step S512, the generated RF energy is applied to the patient.

At step S514, feedback regarding the application of the RF energy to the patient is received by the RF sensors 280. Based on the feedback received by the RF sensors 280, the HLA, at step S516, determines whether a different mode of operation is required. If YES, processing proceeds to step S518. If NO, processing proceeds to step S522. At step S518, the HLA determines whether a different CFG file is required to control the generator 200 to operate in a different mode. If YES, processing returns to step S506 where a new CFG file is selected and loaded based on the desired mode of operation. If NO, processing proceeds to step S520.

At step S520, the loaded CFG file is modified by the HLA to slightly adjust its parameters. For example, based on the feedback received by RF sensors 280, the HLA may determine that the generated RF energy is to be adjusted. In such a case, the HLA may modify the CFG file to adjust the generated RF energy profile instead of loading a new CFG file. After the CFG file has been modified, processing returns to step S508 where the HLA is executed by the HLA engine using the modified CFG file. In embodiments, the generator 200 at step S520 may also receive another HLA in response to the detected feedback, thus moving back to S502.

At step S522, which is reached if it is determined at step S516 that a different mode of operation is not required, the HLA determines whether additional RF energy generation is required. If YES, processing returns to step S510 where the power supply 227 and the RF amplifier 228 is controlled to generate additional RF energy according to the RF energy profile associated with the loaded CFG file. If NO, processing ends.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for operating an electrosurgical generator, the method comprising:
    receiving a high level algorithm at an electrosurgical generator including a processor, a power supply, and a radio frequency amplifier, the high level algorithm including an interpreted language script;
    processing the interpreted language script through an interpreter engine executed by the processor;
    selecting at least one of a plurality of configuration files stored in the electrosurgical generator based on the interpreted language script to effect a desired mode of operation;
    executing the interpreted language script based on the selected one of the plurality of configuration files to generate instructions which cause the electrosurgical generator to control at least one of the power supply and the radio frequency amplifier to generate radio frequency energy according to the selected one of the plurality of configuration files;
    measuring, at a sensor coupled to the radio frequency amplifier, at least one property of the radio frequency energy; and
    selecting another mode of operation based on the at least one property of the radio frequency energy.

2. The method according to claim 1, wherein selecting one of a plurality of configuration files includes selecting a second one of the plurality of configuration files based on the selected another mode of operation.

3. The method according to claim 2, further comprising:
    selecting the second one of the plurality of configuration files based on the interpreted language script to effect the selected another mode of operation; and
    executing the interpreted language script based on the selected second one of the plurality of configuration files to generate instructions which cause the electrosurgical generator to control at least one of the power supply and the radio frequency amplifier to generate radio frequency energy according to the selected second one of the plurality of configuration files.

4. The method according to claim 1, further comprising:
    modifying the selected one of the plurality of configuration files to generate a modified configuration file; and
    executing the interpreted language script based on the modified configuration file to generate instructions which cause the electrosurgical generator to control at least one of the power supply and the radio frequency amplifier to generate radio frequency energy according to the modified configuration file.

5. A system for operating an electrosurgical generator, the system comprising:
    an external download source configured to provide a high level algorithm to the electrosurgical generator; and
    the electrosurgical generator including a power supply, a radio frequency amplifier configured to generate radio frequency energy, a sensor coupled to the radio frequency amplifier and configured to measure at least one property of the radio frequency energy, a processor, and a memory, the processor configured to:
- receive the high level algorithm from the external download source, the high level algorithm including an interpreted language script;
- process the interpreted language script through an interpreter engine executed by the processor;
- select at least one of a plurality of configuration files stored in the memory based on the interpreted language script to effect a desired mode of operation;
- execute the interpreted language script based on the selected one of the plurality of configuration files to generate instructions which cause the electrosurgical generator to control at least one of the power supply and the radio frequency amplifier to generate radio frequency energy according to the selected one of the plurality of configuration files; and
- select another mode of operation based on the at least one property of the radio frequency energy.

6. The system according to claim 5, wherein selecting one of a plurality of configuration files includes selecting a second one of the plurality of configuration files based on the selected another mode of operation.

7. The system according to claim 6, wherein the processor is further configured to:
- select the second one of the plurality of configuration files based on the interpreted language script to effect the another mode of operation; and
- execute the interpreted language script based on the selected second one of the plurality of configuration files to generate instructions which cause the electrosurgical generator to control at least one of the power supply and the radio frequency amplifier to generate radio frequency energy according to the selected second one of the plurality of configuration files.

8. The system according to claim 5, wherein the processor is further configured to:
- modify the selected one of the plurality of configuration files to generate a modified configuration file; and
- execute the interpreted language script based on the modified configuration file to generate instructions which cause the electrosurgical generator to control at least one of the power supply and the radio frequency amplifier to generate radio frequency energy according to the modified configuration file.

9. An electrosurgical generator comprising:
a power supply, a radio frequency amplifier configured to generate radio frequency energy, a sensor coupled to the radio frequency amplifier and configured to measure at least one property of the radio frequency energy, a processor, and a memory, the processor configured to:
- receive a high level algorithm, the high level algorithm including an interpreted language script;
- process the interpreted language script through an interpreter engine executed by the processor;
- select at least one of a plurality of configuration files stored in the memory based on the interpreted language script to effect a desired mode of operation;
- execute the interpreted language script based on the selected one of the plurality of configuration files to generate instructions which cause the electrosurgical generator to control at least one of the power supply and the radio frequency amplifier to generate radio frequency energy according to the selected one of the plurality of configuration files; and
- select another mode of operation based on at least one property of the radio frequency energy.

10. The electrosurgical generator according to claim 9, wherein selecting one of a plurality of configuration files includes selecting a second one of the plurality of configuration files based on the selected another mode of operation.

11. The electrosurgical generator according to claim 10, wherein the processor is further configured to:
- select the second one of the plurality of configuration files based on the interpreted language script to effect the another mode of operation; and
- execute the interpreted language script based on the selected second one of the plurality of configuration files to generate instructions which cause the electrosurgical generator to control at least one of the power supply and the radio frequency amplifier to generate radio frequency energy according to the selected second one of the plurality of configuration files.

12. The electrosurgical generator according to claim 9, wherein the processor is further configured to:
- modify the selected one of the plurality of configuration files to generate a modified configuration file; and
- execute the interpreted language script based on the modified configuration file to generate instructions which cause the electrosurgical generator to control at least one of the power supply and the radio frequency amplifier to generate radio frequency energy according to the modified configuration file.

13. The electrosurgical generator according to claim 9, wherein the processor is further configured to select another mode of operation based on at least one of user input or an identifier associated with an instrument coupled to the power supply.

14. The electrosurgical generator according to claim 13, wherein the identifier is selected from the group consisting of a barcode, a radio frequency identification tag, and a storage device.

* * * * *